United States Patent
Morelli et al.

(10) Patent No.: US 6,916,493 B2
(45) Date of Patent: *Jul. 12, 2005

(54) TWO-PART DISINFECTING SYSTEMS AND COMPOSITIONS AND METHODS RELATING THERETO

(75) Inventors: Joseph Morelli, Bothell, WA (US); C. Cayce Warf, Jr., Woodinville, WA (US); Maura Aldrich, Bellevue, WA (US); Cecilia Moser Morse, Kirkland, WA (US); Jean Wiley, Woodinville, WA (US)

(73) Assignee: Alcide Corporation, Redmond, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/374,690

(22) Filed: Feb. 25, 2003

(65) Prior Publication Data

US 2003/0180247 A1 Sep. 25, 2003

Related U.S. Application Data

(63) Continuation of application No. 09/859,902, filed on May 16, 2001, now Pat. No. 6,524,624.

(51) Int. Cl.[7] .................. A01N 37/36; A01N 57/10; A01N 25/30; A61L 2/16
(52) U.S. Cl. .................. 424/665; 210/754; 422/29; 422/37; 426/335; 426/532; 510/160; 510/161; 510/382; 510/383; 510/419
(58) Field of Search .................. 424/407, 601–602, 424/605–606, 661, 665, 666, 703, 713–714, 718; 514/553–560, 562, 567–574, 576, 578, 601, 608, 665, 708–711, 887, 964, 970, 973, 975; 210/754; 422/29, 37; 426/335, 532; 510/160, 161, 382, 383, 419

(56) References Cited

U.S. PATENT DOCUMENTS

| | | | |
|---|---|---|---|
| 2,061,617 A | 11/1936 | Downing et al. | 260/156 |
| 2,572,605 A | 10/1951 | Fincke | 260/503 |
| 3,444,191 A | 5/1969 | Nielsen | 260/513 |
| 3,845,114 A | 10/1974 | Sweeney et al. | 260/513 R |
| 4,330,531 A | 5/1982 | Alliger | 424/149 |
| 4,585,482 A | 4/1986 | Tice et al. | 106/15.05 |
| 4,861,514 A * | 8/1989 | Hutchings | 510/102 |
| 4,963,287 A * | 10/1990 | Hutchings et al. | 510/101 |
| 5,185,161 A | 2/1993 | Davidson et al. | 424/665 |
| 5,252,343 A | 10/1993 | Kross | 424/661 |
| 5,820,822 A | 10/1998 | Kross | 422/37 |
| 6,043,391 A | 3/2000 | Berger et al. | 562/41 |
| 6,123,966 A | 9/2000 | Kross | 424/665 |
| 6,379,685 B1 | 4/2002 | Richter et al. | 424/405 |
| 6,436,444 B1 | 8/2002 | Richter et al. | 424/665 |
| 6,524,624 B1 * | 2/2003 | Morelli et al. | 424/665 |

FOREIGN PATENT DOCUMENTS

| | | |
|---|---|---|
| EP | 0 287 074 | 10/1988 |
| EP | 565 134 B1 | 10/1993 |
| EP | 904 693 A1 | 3/1999 |
| WO | WO 99/16309 | 4/1999 |
| WO | WO 99/16418 | 4/1999 |

OTHER PUBLICATIONS

PROMT Abstract, accession No. 83:100151 (1983).*
McCutcheon's Emulsifiers & Detergents, The Manufacturing Confectioner publishing Co., Glen Rock, NJ, vol. 1, North American Edition, 1996, p. 31, entry for "BIO–T–ERGE AS–40".*
Chemical Abstracts 105: 29821, abstracting JP 61–20557, 1986.
WPIDS (Derwent) abstract, accession No. 1986–301647, abstracting JP 61–223082, 1986.

* cited by examiner

*Primary Examiner*—John Pak
(74) *Attorney, Agent, or Firm*—Seed IP Law Group PLLC

(57) ABSTRACT

A two-part disinfecting systems, as well as disinfecting compositions and methods for making and using the same. The two-part disinfecting system contains a first part and a second part adapted to be mixed to yield an aqueous disinfecting composition, wherein the first part comprises a chlorite and the second part comprises an acid and an optional oxidizable colorant, and wherein the first part, the second part, or both the first and second parts comprise an alpha olefin sulfonate.

44 Claims, 8 Drawing Sheets

TWO-PART DISINFECTING SYSTEMS AND COMPOSITIONS AND METHODS RELATING THERETO

CROSS-REFERENCE TO RELATED APPLICATION

This application is a continuation of U.S. patent application Ser. No. 09/859,902 filed May 16, 2001 which is now U.S. Pat. No. 6,524,624, which application is incorporated herein by reference in its entirety.

BACKGROUND OF THE INVENTION

1. Field of the Invention

The present invention relates to two-part disinfecting systems, as well as disinfecting compositions and methods for making and using the same, and in a particular embodiment to a two-part disinfecting system that, when mixed, yields a disinfecting composition having reduced chlorine dioxide generation and extended color longevity.

2. Description of the Related Art

Many diseases arise from the growth and spread of microorganisms that can affect all aspects of life, from human health, to animal health, to food and water safety, to the safety of the environments we live in. Disinfectants have found wide spread application in all these areas. Hospitals perform rigorous programs to disinfect and sterilize their environments. Consumer homes are replete with disinfectant hand cleaners, sprays, hard surface cleaners, disinfectant wipes, and fruits and vegetable washes. Disinfectants are widely used on farms where the difference between healthy and sick animals can mean the difference between profitability and loss.

Mastitis is one of the most common and economically costly diseases confronting milk producers. Economic losses result from poorer milk quality, lower milk production, and potential culling of chronically infected animals. The use of disinfectant solutions both before and after milking has found great success in preventing mastitis, particularly disinfectants based on acidified chlorite as commercially available from Alcide Corporation (Redmond, Wash.).

Acidified chlorite (AC) disinfectants are commonly two-part products having a first or "base" part containing a chlorite (such as sodium chlorite) and a second or "activator" part containing an acid activator. The AC disinfectant is formed upon mixing the first and second parts, and typically only in amounts sufficient for a given milking period. Depending upon the desired characteristics and/or intended use of the AC disinfectant, either the first or second part, or both parts, may contain one or more optional ingredients such as skin conditioners, healing agents, surfactants, thickeners, film-forming agents, and/or preservatives. Also, depending upon the two-part system, the AC disinfecting composition may be formed by simply mixing the first and second parts, often in approximately equal volumes, or may involve some additional dilution step before or after mixing.

Color has proved to be an important attribute for teat disinfectants, allowing farmers to visually confirm that the disinfectant has been properly applied to the teat. This is particularly advantageous for confirming application to large herds when multiple farm workers are applying the disinfectant to many different animals. Unfortunately, many such colorants used to impart the color are subject to chemical degradation upon formation of the AC disinfectant. This leads to ineffective coloration as the disinfectant ages— that is, from the point in time following mixing of the first and second parts to form the AC disinfectant.

Teat disinfectants are generally considered animal "drugs" in most countries, and thus controlled by the regulatory agencies overseeing the same. Most often, the only colorants that can be used in a teat disinfectant are those dyes that have been approved for use in food or drugs. For example, in the United States approved dyes can be found in 21 C.F.R. §70.3. When present in an AC disinfectant, these dyes are susceptible to chemical oxidation and rapidly lose their color following formation of the disinfectant.

Previous attempts to address this problem have largely focused on use of pigments as opposed to dyes (see e.g., WO 99/16418, WO 99/16309 and EP 0 904 693 A1). Pigments are insoluble colorants and less susceptible to chemical degradation within the AC disinfectant. However, pigments are plagued by problems associated with settling out of solution, staining parlor floors, and clogging milk filters. In addition, such pigments are not approved in some countries for use in teat disinfectants since they are not approved for food or drug use by their regulatory agencies.

Accordingly, there remains a need in the art for improved AC disinfectants generally, as well as a need for improving the color longevity of dyes within AC disinfectants, particularly those dyes that have been approved for use in food and drugs. The present invention fulfills these needs and provides further related advantages.

BRIEF SUMMARY OF THE INVENTION

In one embodiment, the present invention provides a two-part disinfecting system comprising a first part and a second part adapted to be combined to yield an aqueous disinfecting composition. The first part comprises a chlorite and the second part comprises an acid and an optional oxidizable colorant. In addition, the first part, the second part, or both the first and second parts further comprise an alpha olefin sulfonate. The alpha olefin sulfonate may be in a protonated form (i.e., sulfonic acid), a salt form, or a mixture thereof, and generally contains from 6 to 26 carbon atoms.

When combined, the first part and second part form a disinfecting composition having utility over a wide range of applications. The alpha olefin sulfonate has surprisingly been found to reduce the generation of chlorine dioxide, providing a disinfecting composition that is safer, longer lasting, and with less noxious odors. When the optional oxidizable colorant is present, this results in a disinfecting composition having extended color longevity. Such compositions are particularly useful as teat dips, as well as for other disinfecting applications where extended color longevity is desirable.

In a further embodiment, a method for making a disinfecting composition is disclosed by combining the first part and the second part of the two-part disinfecting system. Such combination may involve mixing liquid forms of the first part and second part, or may involve diluting or dissolving the first part and/or second part prior to mixing, at the time of mixing, and/or after mixing.

In yet another embodiment, a method for disinfecting a substrate is disclosed by contacting the substrate with an effective amount of a disinfecting composition of this invention. Such substrates include any surface, material, or fluid that would benefit from being disinfected, including the skin or tissue of a warm-blooded animal, in particular the teat of a dairy cow, goat or sheep, as well as hard surfaces generally and food surfaces such as meat and meat parts (including beef, poultry, pork, other generally recognized red meats, and fish), fruits and vegetables, and process waters, such as flume waters, cooling tower waters, equipment, and facility cleaning solutions, etc.

These and other aspects of this invention will be evident upon reference to the following detailed description of the invention.

DETAILED DESCRIPTION OF THE INVENTION

Figure 1:
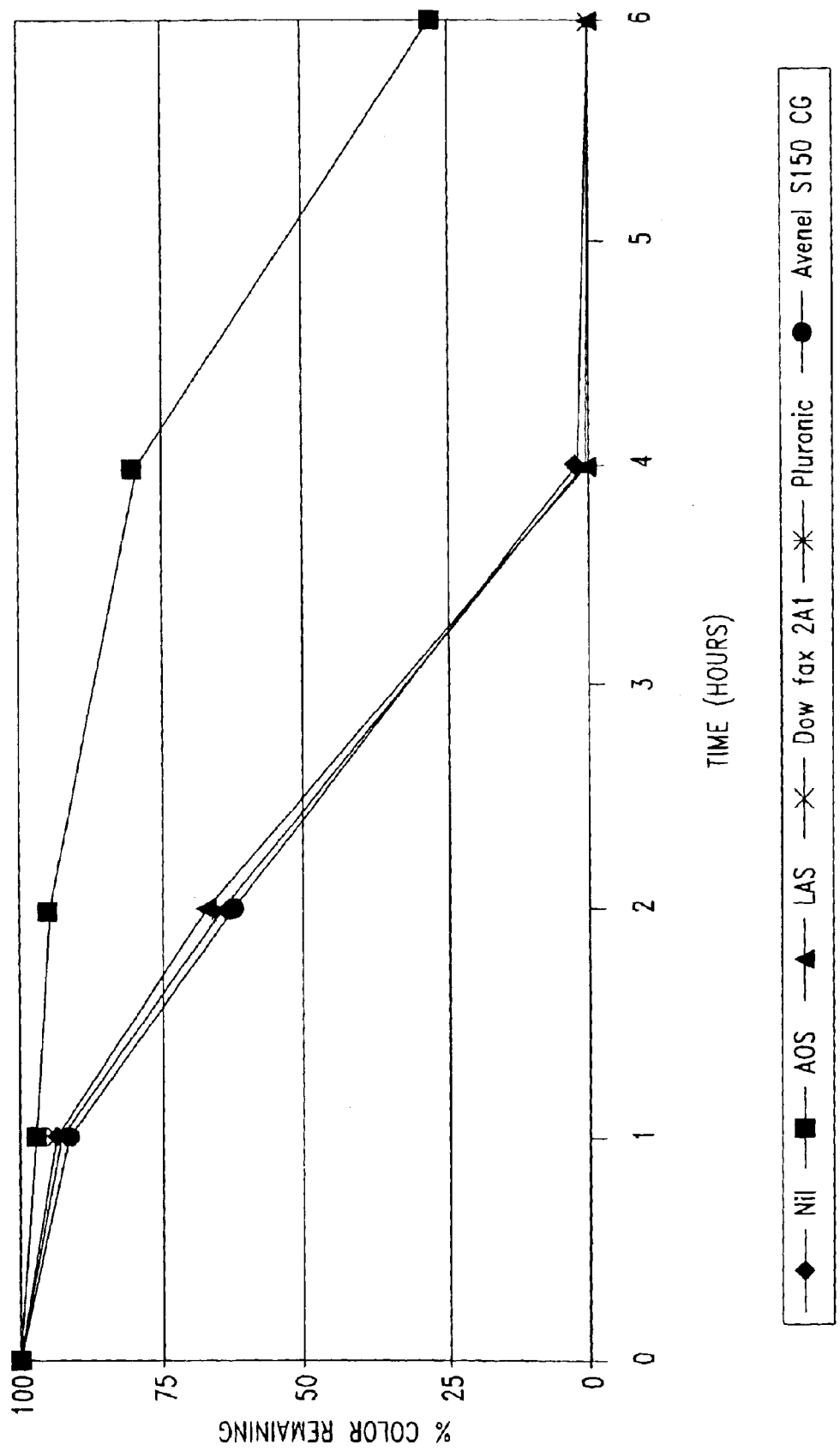
FIGS. 1 and 2 illustrate extended color longevity achieved by a representative disinfecting composition of this invention employing an alpha olefin sulfonate (AOS) as compared to other surfactants.

As noted above, in one embodiment a two-part disinfecting system is disclosed comprising a first part and a second part adapted to be combined to yield an aqueous disinfecting composition. The first part comprises a chlorite and the second part comprises an acid and an optional oxidizable colorant. In addition, the first part, the second part, or both the first and second parts, further comprise an alpha olefin sulfonate.

Acidified chlorite compositions may be generated by combining chlorite (i.e., $ClO_2^-$), typically in the form of a metal salt such as sodium chlorite, with an acid activator. Such compositions are effective disinfectants due to the generation of antimicrobial oxidants, particularly chlorous acid (i.e., $HClO_2$). Chlorous acid is formed very rapidly upon acidification of chlorite in an equilibrium process governed by the solution pH. Chlorous acid can subsequently undergo a series of chemical reactions to form chlorine dioxide. Although not wishing to be limited by the following theory, it is believed that the alpha olefin sulfonate reduces generation of chlorine dioxide upon formation of the disinfecting composition by affecting the rate by which chlorous acid is converted to chlorine dioxide. When an oxidizable colorant is present, it is degraded in significant part by the chlorine dioxide generated within the disinfectant. Thus, the alpha olefin sulfonate, by controlling chlorine dioxide generation, imparts extended color longevity to the disinfecting composition by limiting oxidation of the colorant. Chlorine dioxide is a particularly pungent gas that can be unpleasant and unhealthy at excessive levels in air. Unlike chlorous acid, which stays in solution at the surface being disinfected, chlorine dioxide can escape into the air around the user. Slowing the rate of chlorine dioxide formation leads to a longer lasting disinfectant composition with less noxious odors to the user.

The first and second parts may both be in the form of an aqueous solution, emulsion, microemulsion, cream or gel, or one or both may be in a concentrated, non-aqueous or solid form. For example, the first and second parts may be aqueous solutions or gels to be mixed in approximately equal volumes to form the disinfecting composition, or may be concentrates or solids to be diluted by or dissolved in water, and then mixed to yield the disinfecting composition. Alternatively, the first and/or second parts may be in a non-aqueous or solid form (such as a powder or tablet) to be mixed with or dissolved in water prior to combination. To avoid excessive generation of chlorine dioxide, which may occur upon combination of concentrated forms, it is preferable to mix the first and second parts after the parts are diluted with or dissolved in water.

The chlorite of the first part is typically an alkali or alkaline earth metal chlorite, such as potassium or sodium chlorite, and more typically sodium chlorite. The chlorite is present in the first part in an amount such that, when combined with the second part, it is present within the disinfecting composition at a concentration ranging from about 0.005% to about 3% by weight, generally from 0.05% to 0.5% by weight, and typically from 0.1% to 0.4%.

The acid of the second part is any compound or mixture of compounds that will acidify the chlorite of the first part. In one embodiment, the acid has a pKa ranging from 2 to 5. The acid can be an organic acid, inorganic acid, or mixture thereof. Organic acids include (but are not limited to) formic acid, acetic acid, glycolic acid, lactic acid, pyruvic acid, malic acid, mandelic acid, citric acid, tartaric acid, adipic acid, succinic acid, malonic acid, propionic acid, heptanoic acid, octanoic acid, nonanoic acid, salicylic acid, benzoic acid, gluconic acid, or mixtures thereof. The organic acid can also be alkyl-, alkylarl-, and arylsulfonic acids such as octanesulfonic acid, toluenesulfonic acid, cumenesulfonic acid, dodecylbenzenesulfonic acid, and homo- & copolymers containing poly(styrenesulfonic acid) and poly (acrylamidopropylsulfonic acid). Inorganic acids include (but are not limited to) sulfuric acid, sulfamic acid, phosphoric acid, hydrochloric acid, nitric acid, boric acid, or mixtures thereof. Other acids that may be used include (but are not limited to) hydrated metals salts of iron, aluminum, zirconium, vanadium, and gadolinium as described in U.S. Pat. No. 5,820,822. Acids also include (but are not limited to) solid acid exchange resins, such as Amberlite®, Diaion®, Dowex® and Duolite®, as well as aluminum silicate zeolites. Alternatively, the acid may be any organic acid precursor which forms an acid upon contact with water, such as acid anhydrides, esters, and sulfonate esters. Examples of organic acid precursors are described in U.S. Pat. No. 4,585,482.

The acid is present in the second part in an amount such that, when combined with the first part, it is present within the disinfecting composition at a concentration ranging from about 0.1% to about 10% by weight, generally from 0.5% to 5.0% by weight, and typically from 1.0% to 3.0% by weight.

Alternatively, the amount of acid in the second part may be characterized by the pH of the disinfecting composition. In this regard, the acid is present in the second part in an amount such that, when combined with the first part, the pH of the disinfecting composition is below 5, generally from 2 to 5, and typically from 2.3 to 3.5.

The optional oxidizable colorant of the second part is a colorant that undergoes color loss upon contact with chlorine dioxide at concentrations generally encountered in acidified chlorite disinfectants. Such colorants are typically soluble in vehicles which may be used as carriers for the second part, including (but not limited to) water, alcohol, glycerin and/or oil. In the practice of this invention, either a single oxidizable colorant, or a mixture of two or more oxidizable colorants, may be present in the second part. The amount of oxidizable colorant present in the second part is an amount that, upon combination with the first part, will impart the desired color and/or color intensity to the disinfecting composition.

In the United States, colorants for use in foods and/or drugs are generally classified by the Food and Drug Administration (FDA) as either (1) a food, drug and cosmetic (FD&C) colorant, (2) a drug and cosmetic (D&C) colorant, or (3) an externally applied drug and cosmetic (Ext. D&C) colorant. These colorants may be identified using Colour Index Numbers (CI#) established by the Society of Dyers and Colourists (UK) and the American Association of Textile Chemists & Colorists (Color Index, Society of Dyers and Colorists and American Association of Textile Chemists & Colorists, Rev. $3^{rd}$ ed, Branford, 1975).

Representative FD&C colorants include (but are not limited to) FD&C Blue #1 (CI#42090), FD&C Blue #2 (CI#73015), FD&C Green #3 (CI#42053), FD&C Red #3, FD&C Red #4 (CI#14700), FD&C Red #40 (CI#16035), FD&C Yellow #5 (CI#19140), FD&C Yellow #6 (CI#15980), Orange B, and Citrus Red #2.

Representative D&C colorants include (but are not limited to) D&C Violet #2 (CI#61565), D&C Green #5 (CI#61570), D&C Green #6 (CI#61565), D&C Green #8 (CI#59040), D&C Orange #4 (CI#15510), D&C Yellow #7, D&C Yellow #8 (CI#45350), D&C Yellow #10 (CI#47005), D&C Yellow #11 (CI#47000), D&C Red #6 (CI#15850), D&C Red #17 (CI#26100), D&C Red #22 (CI#45380), D&C Red #28 (CI#45410), and D&C Red #33 (CI#17200).

Representative Ext. D&C colorants include (but are not limited to) Ext. D&C: Violet #2 (CI#60730), Yellow #7 (CI#10316), Acid Green 1 (CI#10020), Food Yellow 2 (CI#13015), Acid Yellow 36 (CI#13065), Food Yellow 8 (CI#14720), Acid Orange 20 (CI#14600), Food Red 3 (CI#14720), Food Red 2 (CI#14815), Acid Red 88 (CI#15620), Food Orange 2 (CI#15980), Acid Red 26 (CI#16150), Food Red 7 (CI#16155), Food Red 9 (CI#16135), Acid Orange 10 (CI#16230), Acid Red 18 (CI#16255), Acid Red (CI#16290), Acid Red 1 (CI#18050), Acid Red 155 (CI#18130), Acid Yellow 121 (CI#18690), Acid Red 180 (CI#18736), Acid Yellow 11 (CI#18820), Acid Yellow 40 (CI#18950), Acid Yellow 5 (CI#18965), Acid Black 1 (CI#20470), Acid Red 163 (CI#24790), Acid Red 73 (CI#27290), Food Black 2 (CI#27755), Food Black 1 (CI#28440), Direct Orange 34 (CI#40215), Acid Blue 3 (CI#42051), Acid Blue 5 (CI#42052), Green S (CI#44090), and Brown HT (CI#20285).

In addition, oxidizable colorants also include naturally occurring colorants such as red cabbage extract, beet root extract, carminic acid, curcumin, beta carotene, annatto extract, grape skin extract, astaxanthin, canthaxanthin, henna, guaiazulene, and mixtures thereof.

Oxidizable colorants of this invention also include any combination of two or more of the above FD&C, D&C, Ext. D&C, and naturally occurring colorants. Furthermore, the oxidizable colorant may, upon contact with the first part, undergo a change in color. Such color change maybe attributable, for example, to a change in pH going from the pH of the second part to the pH of the resulting composition. Alternatively, the first part may optionally contain a colorant such that, when combined with the second part, the resulting composition has a color different from either first and second parts.

As noted above, it has been surprisingly found that the presence of an alpha olefin sulfonate in either the first part, the second part, or both the first and second parts, reduces the generation of chlorine dioxide in the resulting disinfecting composition. As a result, when the optional oxidizable colorant is present, the alpha olefin sulfonate imparts enhanced color longevity to the disinfection composition. As used herein, an "alpha olefin sulfonate" refers to a class of commercial products named according to their use of alpha olefin as a starting material, and are typically produced by sulfonation of an alpha olefin by reaction with $SO_3$ (see, e.g., U.S. Pat. Nos. 2,061,617; 2,572,605; and 3,444,191). As discussed in greater detail below, alpha olefin sulfonates of this invention include alkene sulfonic acids (also referred to herein as the "protonated" form of alpha olefin sulfonate), salt forms of alkene olefin sulfonic acids, and mixtures of both the protonated and salt forms. In this regard, one skilled in this field will appreciate that, in an aqueous solution, an alpha olefin sulfonate, in either the protonated or salt form, will exist in equilibrium with a corresponding counterion, with the relative amount of each being depend upon the pH of the aqueous solution.

An alpha olefin is an alkene that is substantially linear and has a double bond at one end of the molecule. Olefins used for conversion to alpha olefin sulfonates are generally straight chain alpha olefins, but can also include straight chain internal olefins—that is, wherein the initial alkene double bond not at one end of the molecule. Sulfonation of olefins with $SO_3$, after hydrolysis of the resulting sulfones, yields approximately a 50/50 mixture of hydroxy alkane sulfonic acid and alkene sulfonic acid (see, e.g., U.S. Pat. No. 3,845,114). Hydroxy alkane sulfonic acid is converted to alkene sulfonic acid via repeated dehydration and hydrolysis.

In a linear form, the general formula for alkene sulfonic acid is $CH_3(CH_2)_n CH=CH(CH_2)_m SO_3H$ (see, e.g., U.S. Pat. No. 6,043,391), wherein the total number of carbon atoms is the total number of methylene carbon atoms (i.e., n+m) plus the single methyl carbon atom plus the two alkenyl carbon atoms (i.e., n+m+3). In general, the number of carbon atoms for alpha olefin sulfonates range from 6 to 26. In other embodiments, the number of carbon atoms range from 12 to 18, or from 14 to 16. During the sulfonation reaction, the double bond can end up at different locations along the hydrocarbon chain. The resulting alkene sulfonic acid may then be neutralized to form various salts, such as potassium, sodium, magnesium, monethanolamine, or triethanolamine salts. Such salt forms are sold commercially for a variety of applications or are formed during formulation, most notably for use as surfactants.

The alpha olefin sulfonate is present in the first part, the second part, or both the first and second parts in an amount such that, when the first part and second part are combined, it is present within the disinfecting composition at a concentration ranging from about 0.005% to about 50% by weight, generally from 0.05% to 10% by weight, and typically from 0.1% to 5% by weight. Mixtures of alpha olefin sulfonates are also encompassed within this invention. For example, one type of alpha olefin sulfonate may be present in the first part, with a different type present in the second part. Representative alpha olefin sulfonates include (but are not limited to) sodium C12-14 olefin sulfonate (Marlinat SRN 30, Huls AG), sodium C14–16 olefin sulfonate (Bio-Terge AS-40, Stepan), sodium C14–18 olefin sulfonate (Lowenol 0-11016, Lowenstein), and sodium C16–18 olefin sulfonate.

Various optional ingredients may also be present in the first part, the second part, or both first and second parts of the two-part system. Such ingredients include (but are not limited to) wetting agents, textural modifiers, film-forming polymers, surfactants, colorants and mixtures thereof. The wetting agents facilitate contact of the disinfecting composition with the skin or surface, and can be selected from those materials recognized to provide this effect, in both identity and amount. Textural modifiers are those materials which primarily affect the body of the mixed disinfecting composition in terms of retention, flow and lubricity. These include thickening agents such as alkyl celluloses, alkoxy celluloses, xanthan gum, guar gum, and polyacrylamide derivatives, of which the polymer of 2-acrylamido-2-methylpropane sulfonic acid is a preferred example. Inorganic thickening agents include hectorite, synthetic hectorite, magnesium aluminum silicate, bentonite, montmorillonite, and amorphous silicon dioxide. Thickening can also be achieved by a combination of an alpha olefin sulfonate with amphoteric or zwitterionic surfactants and salt. Other textural modifiers include lanolin derivatives, acyl lactylates, polyethylene glycol, glyceryl esters, and mixtures thereof. Skin conditioning and skin healing agents include glycerin, sorbitol, pyrrolidone carboxylic acid, mineral oils, silicone oils, protein hydrolysates, petrolatum, hydrocarbon emollient alcohols and esters, allantoin, and urea. Film-forming polymers include the above-referenced polyacrylamides, as well as the class of poly(vinyl alcohols/ vinyl acetates), polyurethanes, chitosan, polyvinyl pyrrolidone, and polyvinyl pyrrolidone copolymers.

In a further embodiment, a method for disinfecting a substrate is disclosed, wherein the method comprises contacting the substrate with an effective amount of the disinfecting composition formed by combining the first part and the second part of the two-part disinfecting system of this invention. In this context, the substrate may be any surface or material in need of, or that would benefit from, such disinfection, including (but not limited to) skin or tissue, as well as body fluids and mucosal membranes. For example, the substrate may be a wound where disinfection would aid healing. The substrate may be the inside of an animal's mouth where disinfection would help prevent gingivitis and halitosis. The substrate may include any item that is intimately placed in, on, or around the body of an animal, such as dentures, braces, and contact lenses. In a specific application, the substrate is the teat of a dairy cow, goat or sheep. In addition, the substrate may be any surface of a food product, such as meat, fish, fruits and vegetables. The substrate may also include food contact surfaces, and non-food contact surfaces in food processing plants. The substrate may include any hard surface, such as (but not limited to) floors, walls, countertops, containers, instruments and/or equipment found in homes, hospitals, and manufacturing facilities. In a specific application, the hard surfaces may include housing and equipment surfaces in animal rearing and production environments. Materials that may benefit from disinfection include, for example, process waters, such as flume waters, cooling tower waters, livestock drinking waters, equipment and facility cleaning solutions.

In a further aspect of this invention, this invention is directed to a method for making a disinfecting composition comprising combining the first part and the second part of the two-part disinfecting system. In one embodiment, the first and second parts are both aqueous solutions, emulsions, microemulsions, creams or gels, and may be adapted to be combined in equal or different volumes. In another embodiment, at least one of the first or second parts is in a concentrated, non-aqueous or solid form, and the concentrated, non-aqueous or solid form is first diluted with or dissolved in water, and then combined with the other part. Alternatively, the dilution or dissolving step can occur prior to combination with the other part, or simultaneous with combination.

The following examples are provided for the purpose of illustration, not limitation.

EXAMPLES

Example 1

Representative Two-Part Disinfecting System and Resulting Disinfecting Composition This example illustrates the preparation of a representative disinfecting composition made by combining the first and second parts of a representative two-part disinfecting system.

The first and second parts of the two-part system were as follows:

|  | % w/w |
|---|---|
| Part 1 | |
| Sodium Chlorite | 0.64 |
| Cosmedia (HSP 1180, Cognis) | 15.00 |
| Sodium Hydroxide | 0.50 |
| Na₄EDTA | 0.10 |
| Water | q.s. |
| Part 2 | |
| Lactic Acid | 2.64 |
| AOS (Bioterge AS-40, Stepan) | 0.53 |
| FD&C Yellow #5 | 0.30 |
| Glycerin | 2.50 |
| Hydroxyethylcellulose | 1.00 |
| Isopropanol | 2.00 |
| Sodium Benzoate | 0.05 |
| Water | q.s. | q.s. quantum sufficit

The two parts were then combined using equal volumes to yield a disinfecting composition having a pH of 3.0 and the following ingredients:

| Disinfecting Composition | % w/w |
|---|---|
| Sodium Chlorite | 0.32 |
| Lactic Acid | 1.32 |
| AOS | 0.27 |
| FD&C Yellow #5 | 0.15 |
| Glycerin | 1.25 |
| Cosmedia | 7.50 |
| Hydroxyethylcellulose | 0.50 |
| Isopropanol | 2.00 |
| Sodium Hydroxide | 0.25 |
| Na₄EDTA | 0.05 |
| Sodium Benzoate | 0.02 |
| Water | q.s. |

Example 2

Extended Color Longevity with Comparative Compositions

To measure the effectiveness of the alpha olefin sulfonate to extend color longevity, comparative disinfecting compositions were prepared by the same procedures as set forth in Example 1, but with either (a) no surfactant present (the "nil" control), or (b) one of the surfactants numbered (1)

through (4) below in place of the alpha olefin sulfonate (AOS):

|  | % w/w |
|---|---|
| Part 1 | |
| Sodium Chlorite | 0.64 |
| Sodium Hydroxide | 0.02 |
| Water | q.s. |
| Part 2 | |
| Lactic Acid | 2.64 |
| AOS (Bioterge AS-40, Stepan) | 0.53 |
| FD&C Yellow #5 | 0.30 |
| Water | q.s. |

(1) Sodium linear alkylbenzenesulfonate (LAS) (Nacconol 90G made by Stepan)
(2) Sodium dodecyl diphenyloxide disulfonate (Dowfax 2A1 made by Dow Chemical)
(3) Block copolymer of propylene oxide and ethylene oxide (Pluronic F68 made by BASF)
(4) C12–15-(EO)15-sulfonate (Avenel S 150 CG made by BASF)

FIG. 1 is a graph presenting the results of this comparison, with the first and second parts having been combined at time=0 hours. As shown in FIG. 1, the color loss for the disinfecting compositions that contained a surfactant other than alpha olefin sulfonate, and for the nil control, was significantly faster compared to the disinfecting composition of Example 2. In this experiment, 50% color loss occurred at about 2.5 hours for the nil control and comparative surfactants, while 50% color loss for the disinfectant composition of this invention occurred at about 5 hours or twice that of the comparative compositions.

Example 3

Extended Color Longevity with Comparative Compositions

This example further illustrates the enhanced color longevity achieved with a representative disinfectant composition of this invention. In this experiment, disinfecting compositions were prepared by the same procedures as set forth in Example 2, but with either (a) no surfactant present (the "nil" control), or (b) one of the surfactants numbered (1) through (6) below in place of the alpha olefin sulfonate (AOS):

(1) Sodium linear alkylbenzenesulfonate (LAS)
(Nacconol 90G made by Stepan)
(2) Cocobetaine
(Mackam CB-35 made by McIntyre)
(3) Sodium methyl cocoyl taurate
(Geropon TC-270 made by Rhone Poulenc)
(4) C13-E6 phosphate ester
(Rhodafac RE-610 made by Rhone Poulenc)
(5) Lauryl (C 12) amine oxide
(Mackamine LO made by McIntyre)
(6) Dioctyl sulfosuccinate
(Geropon SS-O-75 made by Rhone Poulenc)

Figure 2:
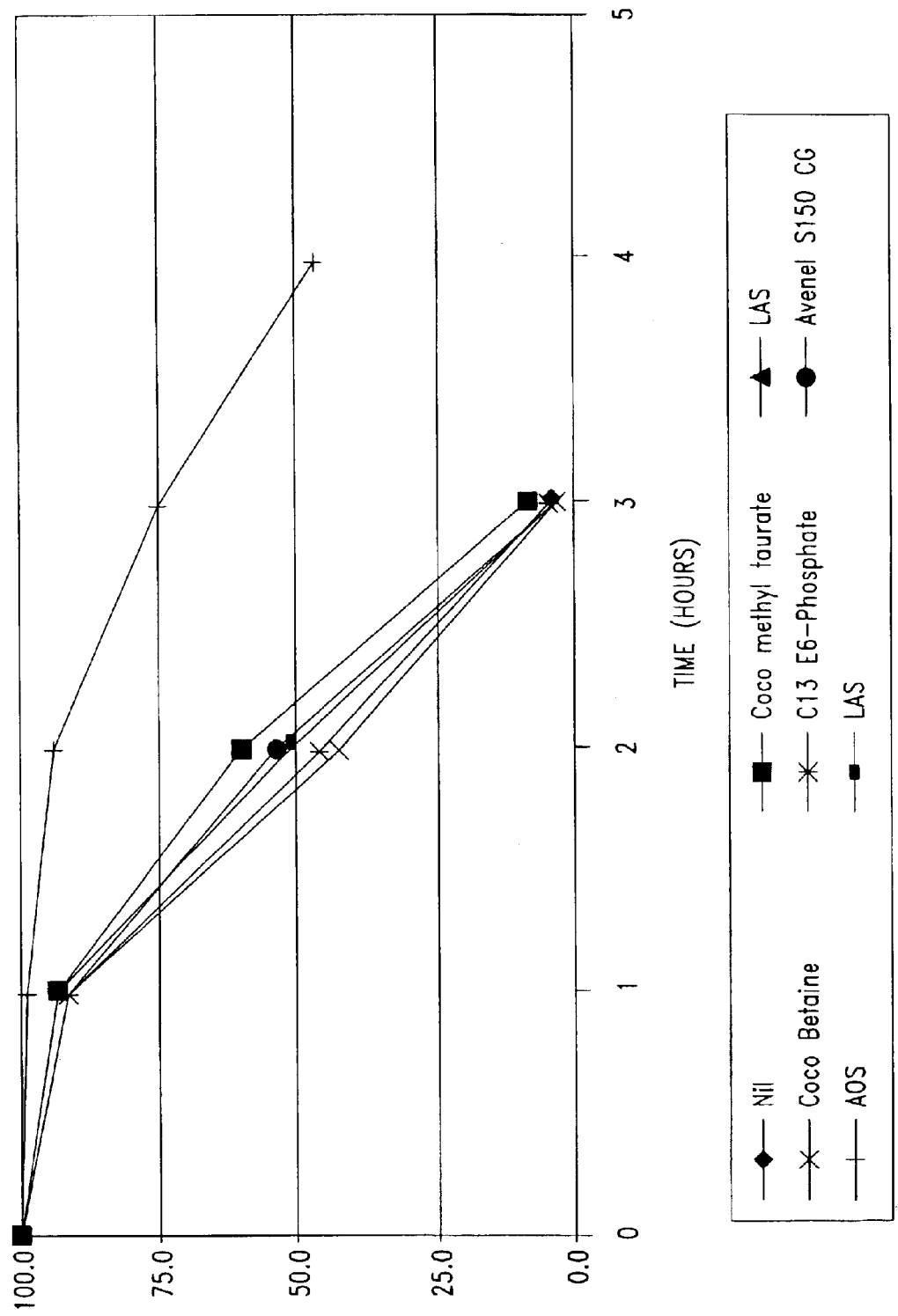

FIG. 2 is a graph presenting the result of this comparison, with the first and second parts having again been combined at time=0 hours. As shown in FIG. 2, the color loss for the disinfecting compositions that contained a surfactant other than alpha olefin sulfonate, and for the nil control, was significantly faster compared to the disinfecting composition of Example 2. In this experiment, 50% color loss occurred at about 2 hours for the nil control and comparative surfactants, while 50% color loss for the disinfectant composition of this invention occurred at about 4 hours or twice that of the comparative compositions.

Example 4

Extended Color Longevity with Surfactant Mixtures

Figure 3:
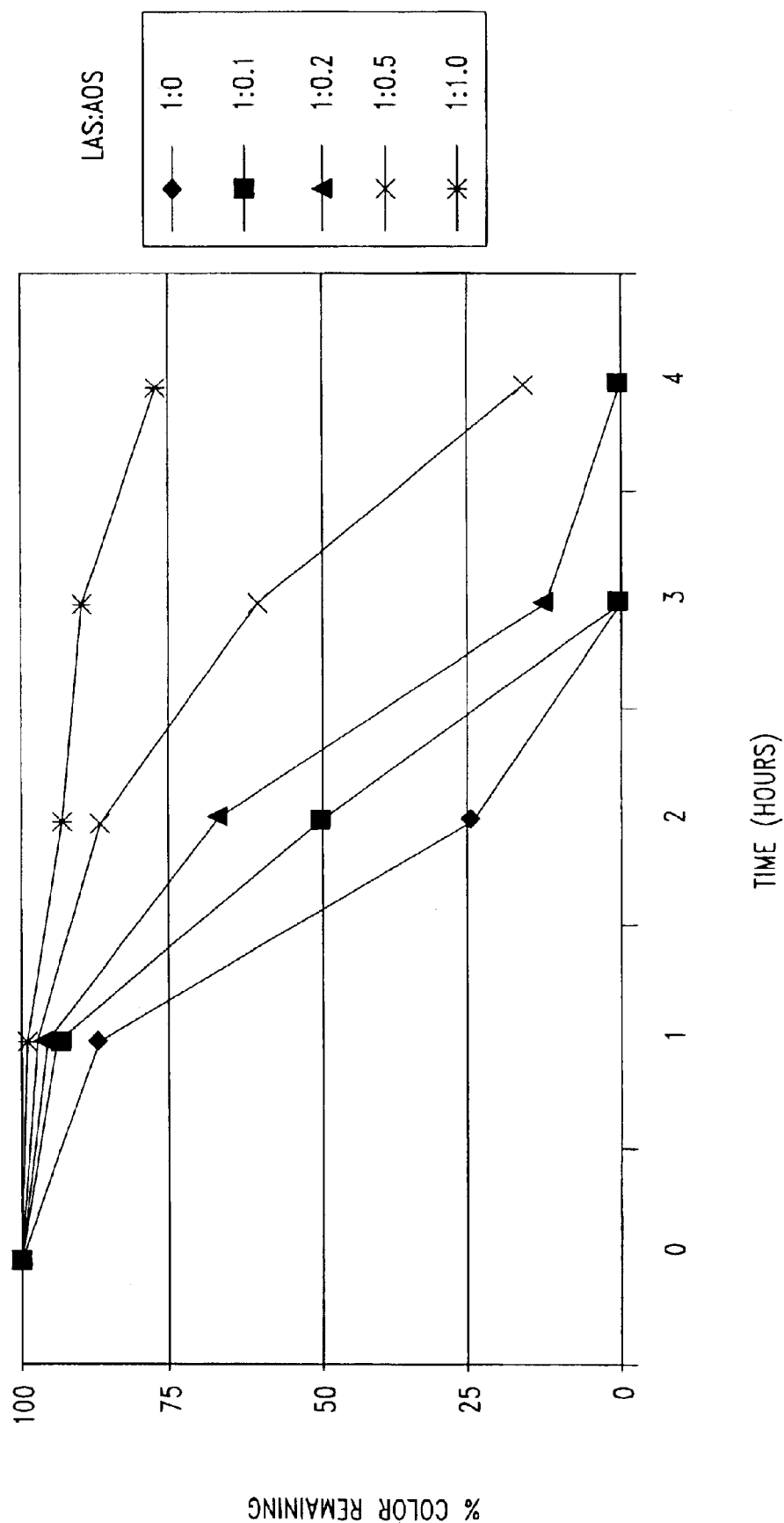
FIG. 3 illustrates extended color longevity achieved with mixtures of an alpha olefin sulfonate (AOS) and another surfactant (LAS) at various ratios of LAS to AOS.

This example illustrates the extended color longevity of disinfectant compositions that contain an alpha olefin sulfonate in combination with a second surfactant, in this case sodium linear alkylbenzenesulfonate ("LAS") (Nacconol 90G made by Stepan). The disinfecting compositions were made in the same manner as set forth in Example 1, but using a mixture of LAS and alpha olefin sulfonate (AOS) at weight ratios (LAS:AOS) of 1:0, 1:0.1, 1:0.2, 1:0.5 and 1:1). FIG. 3 shows the color loss profiles for the disinfecting compositions of this experiment. Note that for the disinfecting composition wherein the ratio of LAS to AOS is 1:1, there is about a 25% color loss after 4 hours, which is comparable to the rate achieved with the disinfecting composition of Example 2.

|  | % w/w |
|---|---|
| Part 1 | |
| Sodium Chlorite | 0.64 |
| Sodium Hydroxide | 0.05 |
| Na₄EDTA | 0.10 |
| Water | q.s. |
| Part 2 | |
| Lactic Acid | 2.64 |
| LAS (Nacconol 90G, Stepan) | 0.50 |
| AOS (Bioterge AS-40, Stepan) | var. |
| FD&C Yellow #5 | 0.30 |
| Glycerin | 5.00 |
| Poly(Vinyl Alcohol/Acetate) | 2.00 |
| (Airvol 08–125, Air Products) | |
| Polyvinyl Pyrrolidone (K-90, ISP) | 0.50 |
| Sodium Benzoate | 0.04 |
| Water | q.s. |

Example 5

Extended Color Longevity with Representative Oxidizable Colorants

Figure 4:
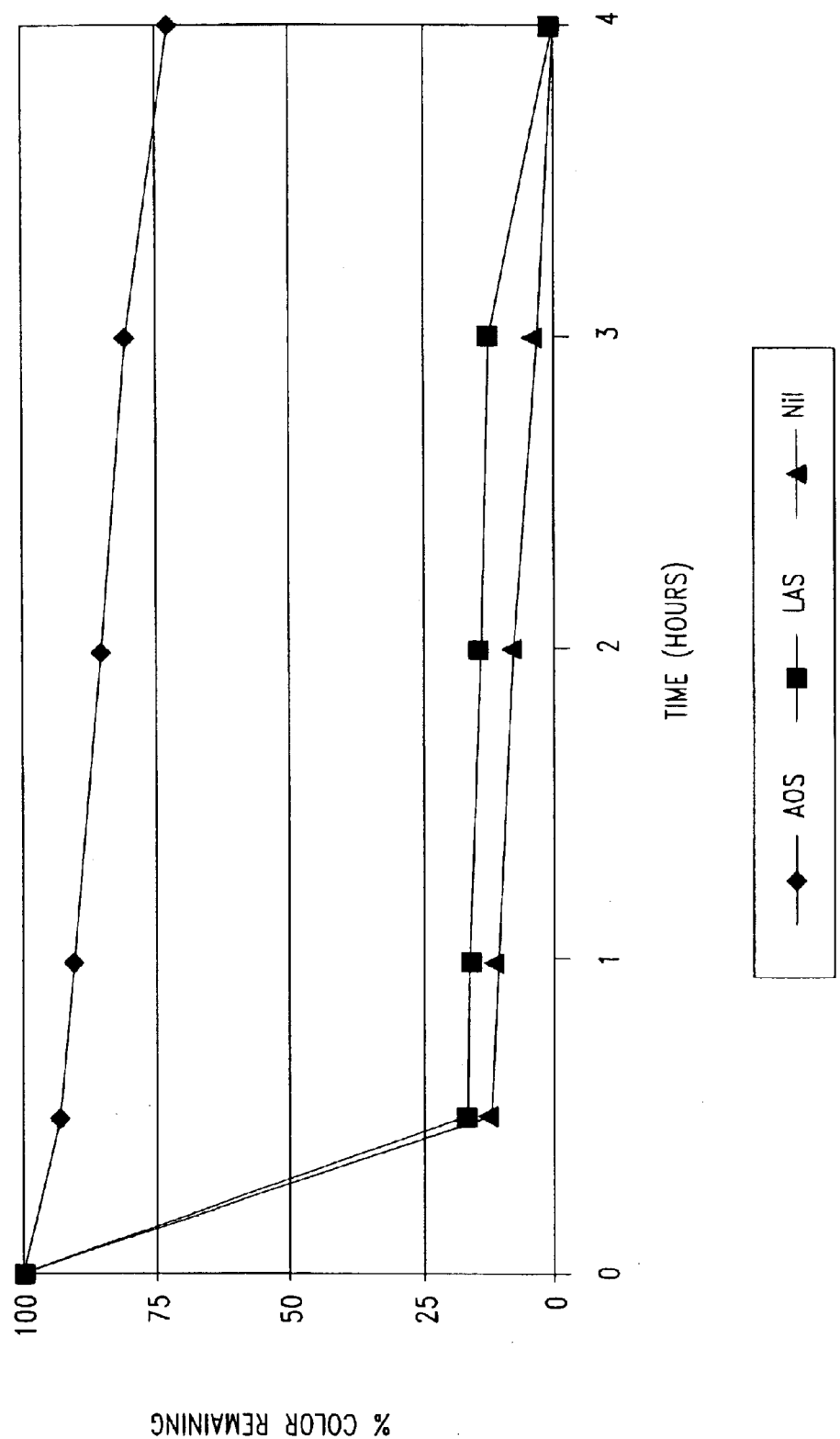
FIGS. 4 and 5 illustrate extended color longevity achieved with representative disinfecting compositions of this invention employing FD&C Red #40 dye (FIG. 4) or FD&C Blue #1 dye (FIG. 5).
Figure 5:
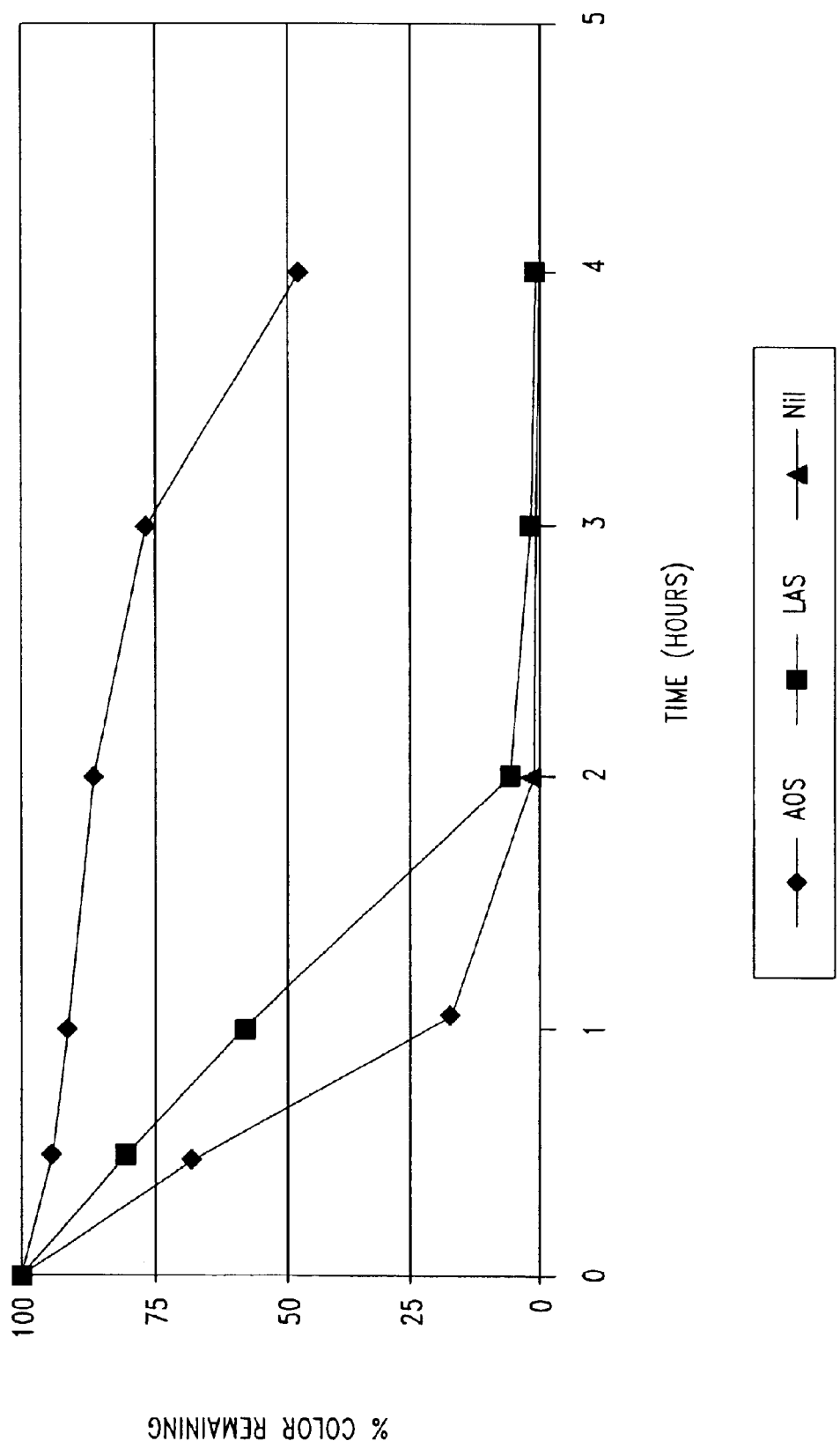

This example illustrates the extended color longevity of disinfecting compositions containing representative oxidizable colorants. The disinfecting compositions of this experiment were made by the same procedures set forth in Example 1, but using the oxidizable colorants FD&C Red #40 or FD&C Blue #1, and containing AOS, LAS or no surfactant. FIGS. 4 and 5 present the results of this experiment for FD&C Red #40 and FD&C Blue #1, respectively. As shown in these figures, the color loss profiles for compositions comprising LAS as the surfactant parallel that of the nil control, regardless of which colorant was employed.

|  | % w/w |
|---|---|
| Part 1 | |
| Sodium Chlorite | 0.64 |
| Water | q.s. |

-continued

| | % w/w |
|---|---|
| Part 2 | |
| Lactic Acid | 2.64 |
| Surfactant (either LAS or OAS) | 1.00 |
| Dye (either FD&C Red #40 or FD&C Blue #1) | 0.30 |
| Water | q.s. |

Figure 6:
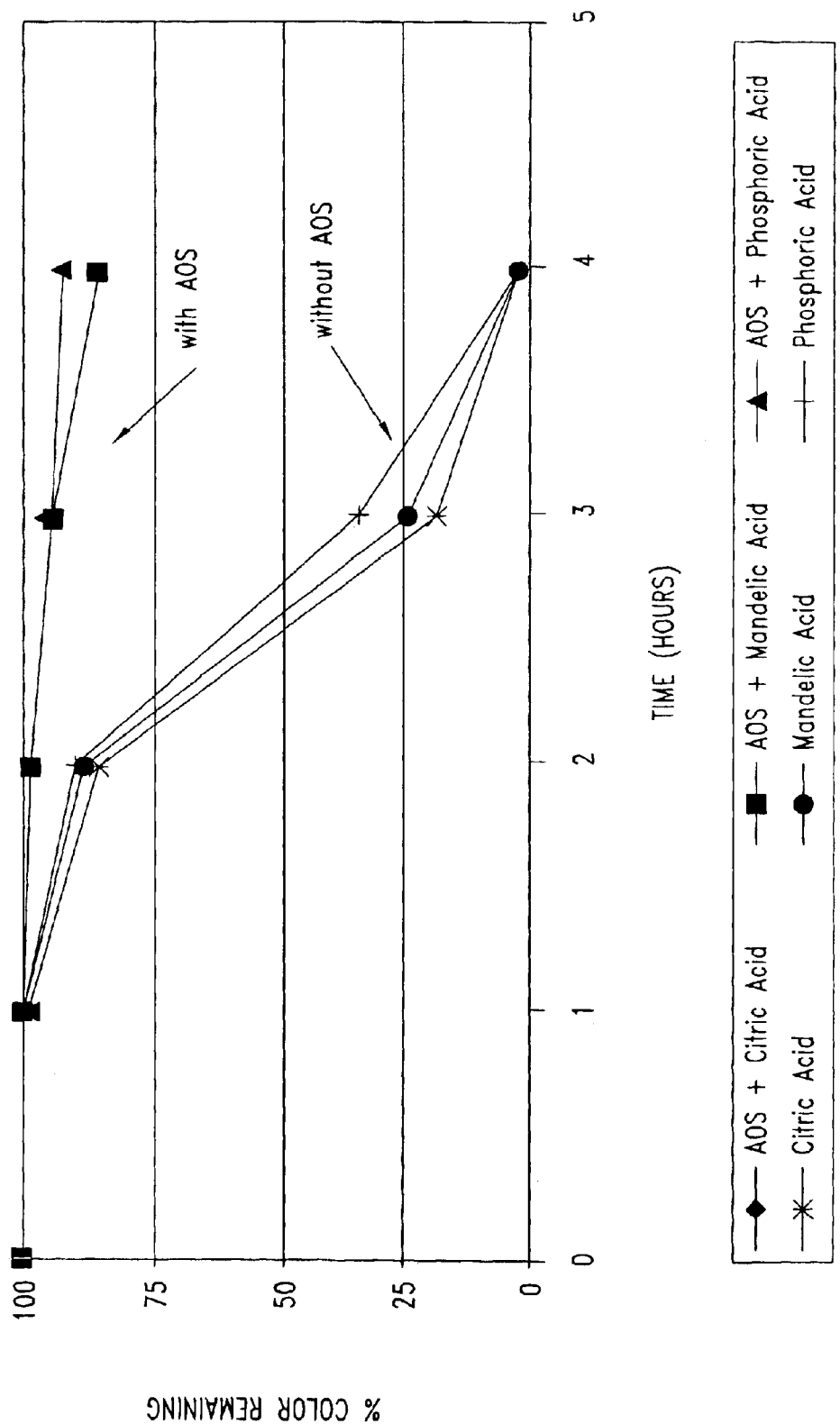
FIG. 6 illustrates reduced chlorine dioxide generation in a representative composition of this invention.

As noted previously, it is believed that AOS inhibits the initial rate of chlorine dioxide generation in the acidified chlorite system, which leads to extended color longevity when the two parts are mixed. When the above experiment is repeated, but in the absence of the oxidizable colorant, the initial rate of chlorine dioxide generation was found to be much less for AOS compared to the nil control and LAS composition. The results of this experiment are present in FIG. 6.

Example 6

Further Representative Two-Part Disinfecting Systems and Resulting Disinfecting Compositions This example illustrates the preparation of further representative disinfecting composition made by combining the first and second parts of a representative two-part disinfecting system. The first and second parts of the two-part system were as follows:

| | % w/w |
|---|---|
| Part 1 | |
| Sodium Chlorite | 0.64 |
| Water | q.s. |
| Part 2 | |
| Acid (see below) | 2.00 |
| AOS (Bioterge AS-4-, Stepan) | 0.53 |
| FD&C Yellow #5 | 0.40 |
| Sodium Hydroxide | var. to achieve pH 2.8 |
| Water | q.s. |

Figure 7:
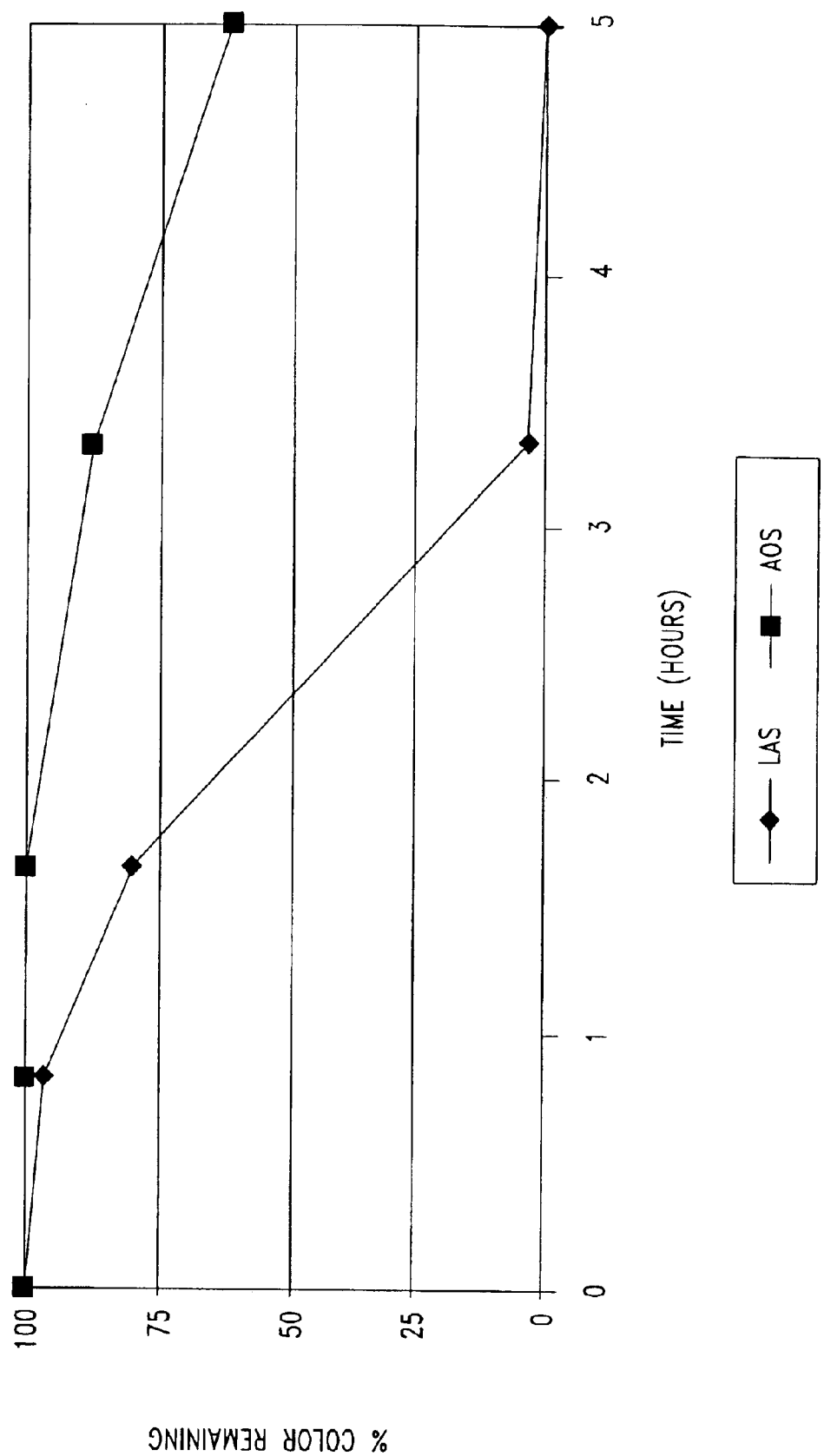
FIGS. 7 and 8 illustrate extended color longevity achieved with representative disinfecting compositions of this invention employing different acids, namely citric acid, mandelic acid or phosphoric acid (FIG. 7), or formic acid (FIG. 8).

Three different acids were used in the second part, namely citric acid, mandelic acid or phosphoric acid. The first part was then combined with each of the three second parts in equal volumes to yield three different disinfecting compositions. FIG. 7 shows the color loss profiles for each of these three disinfecting compositions, compared to the same disinfecting composition without the alpha olefin sulfonate (AOS).

Example 7

Figure 8:
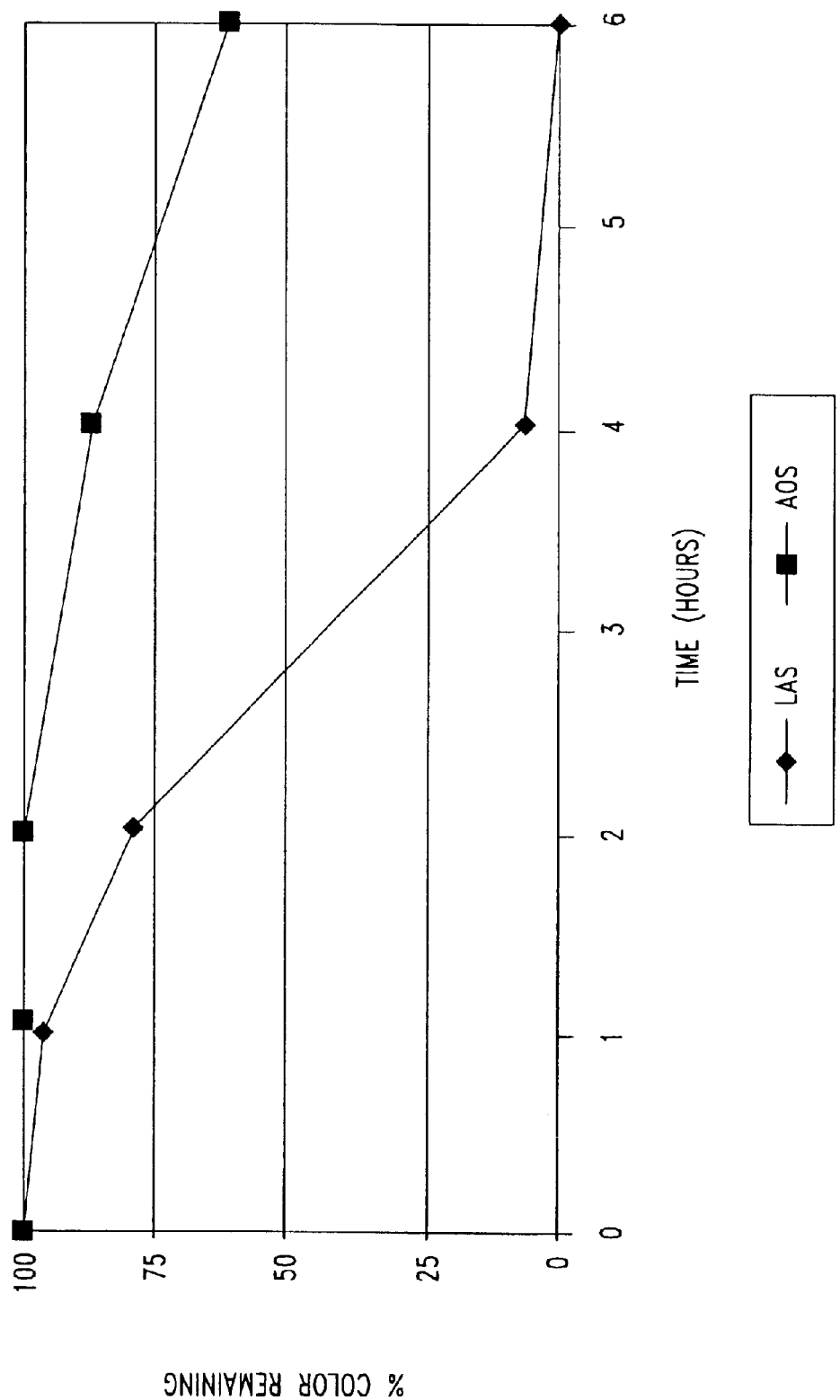

Further Representative Two-Part Disinfecting Systems and Resulting Disinfecting Compositions The experiment in Example 6 was repeated using formic acid, with either AOS or LAS as follows, the results of which are presented in FIG. 8.

| | % w/w |
|---|---|
| Part 1 | |
| Sodium Chlorite | 0.64 |
| Sodium Hydroxide | 0.05 |
| Water | q.s. |
| Part 2 | |
| Formic Acid | 1.33 |
| Surfactant | 0.53 |
| FD&C Yellow #5 | 0.40 |
| Glycerin | 5.00 |
| Sodium Benzoate | 0.04 |
| Poly(Vinyl Alcohol/Acetate) (Airvol 0540S, Air Products) | 2.50 |
| Water | q.s. |

Example 8

Further Representative Two-Part Disinfecting Systems

This example illustrates a further representative two-part disinfecting systems of the present invention, designated system "A" through "E" below.

| | Two-Part System (% w/w) | | | | |
|---|---|---|---|---|---|
| | A | B | C | D | E |
| Part 1 | | | | | |
| Sodium Chlorite | 0.64 | 0.64 | 0.64 | 0.32 | 3.2 |
| AOS | — | — | — | 1.00 | — |
| Cosmedia HSP 1180 | 15.00 | — | — | — | — |
| Xanthan Gum | — | 0.50 | — | — | — |
| Sodium Hydroxide | 0.50 | 0.05 | 0.02 | 0.02 | — |
| Na₄EDTA | 0.20 | 0.20 | 0.04 | — | 0.25 |
| Water | q.s. | q.s. | q.s. | q.s. | — |
| Part 2 | | | | | |
| Lactic Acid | — | 1.50 | 2.64 | 5.20 | — |
| Mandelic Acid | 3.00 | 0.50 | — | — | — |
| Gluconic Acid | — | — | — | — | 15.00 |
| Nonanoic Acid | — | — | — | 0.50 | — |
| Phosphoric Acid | — | — | — | — | 1.20 |
| AOS | 0.50 | 0.27 | 0.50 | — | 5.00 |
| LAS | — | 0.53 | — | 0.50 | — |
| Glycerin | 5.00 | 5.00 | 10.00 | 5.00 | 50.00 |
| Sorbitol | — | — | — | 1.00 | — |
| Polyvinyl Alcohol/Acetate | — | 2.00 | — | — | — |
| Hydroxyethylcellulose | 1.50 | — | — | — | — |
| Polyvinylpyrrolidone | — | 0.50 | — | — | — |
| Xanthan Gum | — | — | — | 0.30 | — |
| Isopropanol | 2.00 | — | — | 2.00 | — |
| FD&C Yellow #5 | 0.30 | 0.30 | 0.30 | 0.50 | 1.50 |
| Potassium Benzoate | 0.05 | 0.04 | 0.04 | — | 0.1 |
| Allantoin | — | — | 0.50 | — | — |
| Potassium Hydroxide | — | — | — | 0.05 | — |
| Water | q.s. | q.s. | q.s. | q.s. | — |

Disinfecting compositions may be formed by combining equal volumes of part 1 with part 2 for each of systems A, B, C and D. For system E, the corresponding disinfecting composition may be generated by combining part 1, part 2 and water in a 1:1:8 volume ratio.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A two-part disinfecting system comprising a first part and a second part adapted to be mixed to yield an aqueous disinfecting composition, wherein the first part comprises a chlorite and the second part comprises an acid, and wherein the first part, the second part, or both the first part and second parts contains an alpha olefin sulfonate, which is present in the first part, the second part, or both the first and second parts in an amount so that, when the first part and second part are combined, it is present within the disinfecting composition at a concentration ranging from about 0.005% to about 50% by weight, and wherein the acid is present in the second part in an amount so that, when combined with the first part, the PH of the disinfecting composition is below 5.

2. The system of claim 1 wherein the alpha olefin sulfonate is introduced into the first part, the second part, or both the first and second parts in an acid form of alpha olefin sulfonate.

3. The system of claim 1 wherein the alpha olefin sulfonate is introduced into the first part, the second part, or both the first and second parts in a salt form of alpha olefin sulfonate.

4. The system of claim 3 wherein the salt form of alpha olefin sulfonate is an alkali metal salt of alpha olefin sulfonate.

5. The system of claim 4 wherein the alkali metal salt of alpha olefin sulfonate is a sodium or potassium salt.

6. The system of claim 1 wherein the alpha olefin sulfonate has from 6 to 26 carbon atoms.

7. The system of claim 1 wherein the alpha olefin sulfonate has from 12 to 18 carbon atoms.

8. The system of claim 1 wherein the alpha olefin sulfonate has from 14 to 16 carbon atoms.

9. The system of claim 1 wherein the alpha olefin sulfonate is present in the first part, the second part, or both the first and second parts in an amount so that, when the first part and second part are combined, it is present within the disinfecting composition at a concentration ranging from 0.05% to 10% by weight.

10. The system of claim 1 wherein the alpha olefin sulfonate is present in the first part, the second part, or both the first and second parts in an amount so that, when the first part and second part are combined, it is present within the disinfecting composition at a concentration ranging from 0.1% to 5% by weight.

11. The system of claim 1 wherein the chlorite is a metal chlorite.

12. The system of claim 11 wherein the metal chlorite is an alkali or alkaline earth metal chlorite.

13. The system of claim 11 wherein the metal chlorite is sodium chlorite or potassium chlorite.

14. The system of claim 11 wherein the metal chlorite is sodium chlorite.

15. The system of claim 1 wherein the chlorite is present in the first part in an amount so that, when combined with the second part, it is present within the disinfecting composition at a concentration ranging from about 0.005% to about 3% by weight.

16. The system of claim 1 wherein the chlorite is present in the first part in an amount so that, when combined with the second part, it is present within the disinfecting composition at a concentration ranging from 0.05% to 0.5% by weight.

17. The system of claim 1 wherein the chlorite is present in the first part in an amount so that, when combined with the second part, it is present within the disinfecting composition at an concentration ranging from 0.1% to 0.4% by weight.

18. The system of claim 1 wherein the acid has a $pK_a$ ranging from 2 to 5.

19. The system of claim 1 wherein the acid is an organic acid.

20. The system of claim 19 wherein the organic acid is glycolic acid, lactic acid, malic acid, mandelic acid, citric acid, tartaric acid, adipic acid, succinic acid, malonic acid, heptanoic acid, octanoic acid, nonanoic acid, benzoic acid, gluconic acid, or a mixture thereof.

21. The system of claim 1 wherein the acid is an inorganic acid.

22. The system of claim 21 wherein the inorganic acid is sulfuric acid, sulfamic acid, phosphoric acid, hydrochloric acid, nitric acid, or a mixture thereof.

23. The system of claim 1 wherein the acid is a mixture of an organic acid and an inorganic acid.

24. The system of claim 1 wherein the acid is present in the second part in an amount so that, when combined with the first part, it is present within the disinfecting composition at a concentration ranging from about 0.1% to about 10% by weight.

25. The system of claim 1 wherein the acid is present in the second part in an amount so that, when combined with the first part, it is present within the disinfecting composition at a concentration ranging from 0.5% to 5.0% by weight.

26. The system of claim 1 wherein the acid is present in the second part in an amount so that, when combined with the first part, it is present within the disinfecting composition at an concentration ranging from 1.0% to 3.0% by weight.

27. The system of claim 1 wherein the acid is present in the second part in an amount so that, when combined with the first part, the pH of the disinfecting composition ranges from 2 to below 5.

28. The system of claim 1 wherein the acid is present in the second part in an amount so that, when combined with the first part, the pH of the disinfecting composition ranges from 2.3 to 3.5.

29. The system of claim 1 wherein the first part and the second part are adapted to be combined in equal volumes.

30. The system of claim 1 wherein both the first part and the second part are in the form of an aqueous solution, emulsion, microemulsion, cream or gel.

31. The system of claim 1 wherein at least one of the first part or the second part is in a concentrated or solid form.

32. The system of claim 1 wherein the first part, the second part, or both the first and second parts further comprise a textural modifier, wetting agent, thickening agent, skin conditioner, healing agent, film-forming polymer, surfactant, preservative, or a mixture thereof.

33. A disinfecting composition formed by combining the first part and the second part of the two-part disinfecting system of claim 1.

34. A method for making a disinfecting composition comprising combining the first part and the second part of the two-part disinfecting system of claim 1.

35. The method of claim 34 wherein both the first part and the second part are in the form of an aqueous solution, emulsion, microemulsion, cream or gel.

36. The method of claim 34 wherein at least one of the first part or second part is in a concentrated of solid form.

37. The method of claim 36 wherein the concentrated or solid form is first diluted with or dissolved in water prior to contact with the other part.

38. A method for disinfecting a substrate comprising contacting the substrate with an effective amount of a disinfecting composition formed by mixing the two-part disinfecting system of claim 1.

39. The method of claim 38 wherein the substrate is skin or tissue of a warm-blooded animal.

40. The method of claim 38 wherein the substrate is a teat of a dairy cow, goat or sheep.

41. The method of claim 38 wherein the substrate is a hard surface.

42. The method of claim 38 wherein the substrate is a food surface or a surface in contact with food.

43. The method of claim 38 wherein the substrate is processing water.

44. The method of claim 38 wherein the substrate is cooling tower water.

* * * * *